United States Patent [19]

Beroff et al.

[11] 4,418,694

[45] Dec. 6, 1983

[54] NON-METALLIC, BIO-COMPATIBLE HEMOSTATIC CLIPS

[75] Inventors: Howard Beroff, Bridgewater; Namassivaya Doddi, Manville; Stephen J. Jewusiak, Denville, all of N.J.

[73] Assignee: Ethicon, Inc., Somerville, N.J.

[21] Appl. No.: 282,461

[22] Filed: Jul. 13, 1981

Related U.S. Application Data

[63] Continuation-in-part of Ser. No. 49,376, Jun. 18, 1979, abandoned.

[51] Int. Cl.³ .................... A61B 17/12; A61B 17/00

[52] U.S. Cl. .................... 128/326; 128/325; 128/346

[58] Field of Search .................... 128/325, 326, 346

[56] References Cited

U.S. PATENT DOCUMENTS

| | | | |
|---|---|---|---|
| 1,983,969 | 12/1934 | Davis | 128/346 |
| 3,175,556 | 3/1965 | Wood et al. | 128/326 |
| 3,247,852 | 4/1966 | Schneider | 128/346 |
| 3,315,679 | 4/1967 | Sarracino | 128/346 |
| 3,323,208 | 6/1967 | Hurley, Jr. | 128/346 |
| 3,825,012 | 7/1974 | Nicoll | 128/346 |
| 3,926,195 | 12/1975 | Bleier et al. | 128/346 |
| 4,016,883 | 4/1977 | Wright, Jr. | 128/346 |

FOREIGN PATENT DOCUMENTS

| | | | |
|---|---|---|---|
| 1957855 | 5/1971 | Fed. Rep. of Germany | 128/325 |
| 1530282 | 10/1978 | United Kingdom | 128/346 |
| 135588 | of 1961 | U.S.S.R. | 128/346 |

OTHER PUBLICATIONS

Ethicon Catalog Featuring Ligaclip® Ligating Clips, ©1973.

*Primary Examiner*—C. Fred Rosenbaum
*Assistant Examiner*—C. W. Shedd
*Attorney, Agent, or Firm*—Robert L. Minier

[57] ABSTRACT

Non-metallic, bio-compatible hemostatic clips of absorbable or nonabsorbable materials are formed by two legs joined with a resilient hinge. One leg terminates in a hook member which secures the other leg when the clip is closed. The clip applier is a forceps-type instrument having channeled jaws especially adapted to receive and close the clip.

4 Claims, 8 Drawing Figures

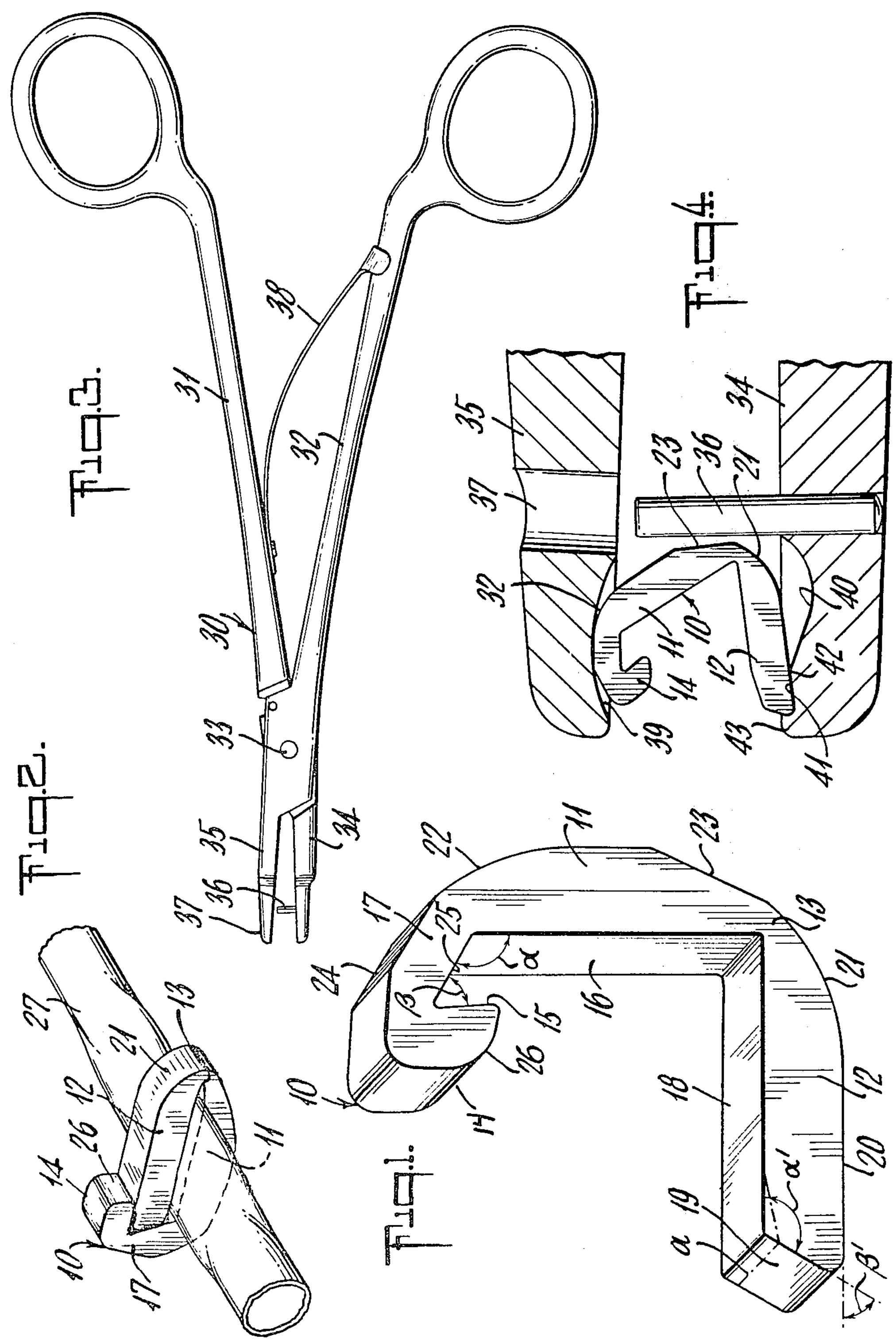

22
10
14
15
16
46
18
11
19
42
43
12

39
35
14
36
22
10
12
43
34
45
44

22
10
14
15
11
16
46
18
19
47
12

35
22
39
14
10
11
12
34
48
49
47

NON-METALLIC, BIO-COMPATIBLE HEMOSTATIC CLIPS

The present application is a continuation-in-part application of our co-pending application Ser. No. 49,376 filed June 18, 1979, now abandoned.

The present invention relates to hemostatic clips and clip appliers, and, more particularly, to hemostatic clips fabricated from polymeric materials which may be absorbable or non-absorbable, and to instruments for applying such clips to blood vessels and the like.

BACKGROUND OF THE INVENTION

In many surgical procedures, it is often necessary to ligate a plurality of vessels within the surgical site. The vessels may then be severed downstream of the ligated portion. In some instances, the vessel may be ligated at two spaced apart areas and the portion of the vessel between the ligations removed. The primary reason for ligating the vessels is to maintain the surgical site free of an excess of blood and to reduce blood loss in the patient. Also in certain surgical procedures wherein tumors or parts of organs and the like are to be removed, the tumor or organ may have to be separated from certain vessels and before separating, the vessels will have to be ligated.

Once a blood vessel is completely shut off, hemostasis; that is, the natural closing of the ligated end of the vessel so as to stop blood flow will occur in several days depending on the vessel. The body, in the meantime, will continue to allow blood to flow around the ligated area through appropriate capillaries and secondary vessels with the natural physiological function of the body enlarging these by-pass vessels until adequate blood flow is attained. Hence, when ligating the vessel, there should be a positive stopping of the blood flow in the main vessel; i.e., no leakage, which might cause blood loss in the patient and may also disrupt the natural hemostasis and concurrent manufacture of new paths of blood flow in the patient.

In the past, this closing of the vessel was usually accomplished using ligatures; i.e., threads or filaments which the doctor tied around the vessel desired to be closed. A very time consuming process and one in which positive closure of the vessel was not always accomplished.

In relatively recent years, hemostatic clips have replaced the ligatures in many surgical procedures to close blood vessels and other small fluid ducts. These hemostatic clips have been narrow U-shaped or V-shaped strips formed of tantalum or stainless steel which are capable of being deformed and possess sufficient strength to retain the deformation when clamped about a blood vessel. The clips are generally applied using a forceps-type device having jaws channeled or otherwise adapted to hold the open clip. Representative hemostatic clips and appliers of the prior art are best illustrated in U.S. Pat. Nos. 3,867,944; 3,631,707; 3,439,523; 3,439,522; 3,363,628; 3,312,216; and 3,270,745.

It has been suggested in the prior art, as in U.S. Pat. No. 3,439,523, for example, that hemostatic clips might be formed of inexpensive plastics or materials which are slowly absorbable in the body. Unfortunately, the very small conventional U-and V-shaped hemostatic clips do not possess the required strength or deformability when constructed of known plastic materials to be successfully clamped about a blood vessel. Thus, although the need and desirability of providing inexpensive plastic hemostatic clips of both absorbable and non-absorbable materials has been recognized for over ten years, there has been no practical way to satisfy this need. To accomplish the positive closing of the vessel with non-metallic, bio-compatible, hemostatic clips, the vessel clamping surfaces of the clips should have a minimal or no gap between the surfaces when the clip is closed. Also, the surfaces should be sufficiently smooth and have large enough areas so as not to sever or even partially sever the closed vessel. The non-metallic, bio-compatible hemostatic clip, once placed in a clamping position on a vessel, must maintain that position for the period of time required for hemostasis to take place. The clip must maintain its strength in vivo to withstand the pressure trying to force the vessel back open for a sufficient period of time to allow for the natural permanent shutting of the vessel.

The configuration of a hemostatic clip is also important. Because the clip is often used in and around the important organs of the body and the clip is left in the body after the surgical procedure is completed, it is important that the clip be configured to keep trauma within the area; i.e., irritation from a foreign object, to a minimum. Smoothness and size of the clip as well as a lack of projections and a minimum of sharp angles, all contribute to reducing the trauma which may occur when placing a foreign object such as a hemostatic clip, within a human body.

The clip configuration is also important to insure the proper placement of a clip. When hemostatic clips are used in a surgical procedure, the general practice is for the nurse to pick up a clip in the jaws of a forceps-type applying instrument. The nurse passes the instrument with the clip in place to the surgeon. The surgeon places the jaws of the instrument into the surgical site and around the vessel to be ligated. In many instances, the surgeon will be placing the jaws of the instrument into areas where the surgeon has limited vision. The surgeon then closes the clip over the vessel to be ligated. All of the handling and manipulation of the instrument must be accomplished without dropping the clip and while maintaining the sterility of the clip.

The size of the clip is also important as the smaller the clip, the less foreign material there is being implanted in the patient. Also, the smaller size allows for more clips to be used in a surgical procedure and in certain instances may simplify the procedure or at least reduce possible side effects resulting from the insertion of foreign objects within the human body.

U.S. Pat. No. 3,926,195 describes a plastic clip designed for the temporary or permanent closing of the oviduct and vas deferens in humans. These clips preferably have a clamping surface of from 6 to 10 mm in length and 3 to 6 mm in width. The size of such clips are accordingly considerably larger than is desirable for hemostatic clips. Additionally, clips of U.S. 3,926,195 require the use of several complex tools to apply the clips which are acceptable for the purposes described in the reference but would be unacceptable in a surgical procedure requiring the rapid placement of a large number of hemostatic clips to stem the flow of blood from severed vessels.

While the importance of the clip to the surgical procedure has been discussed, it should be pointed out that the configuration of the clip is also important to the manufacture of the clip. The configuration should be such as to take advantage of simple and economic means of manufacture of the clip such as injection molding. The configuration should be such as to reduce the production of seconds or malformed clips in the production. Also, the configuration of the clip should be such as to follow for very simple design of the jaws of the applier to reduce cost of the applier while maintaining the required assurance of holding and setting of the clip during the surgical proceedings.

It is accordingly an object of the present invention to provide a plastic hemostatic clip effective for clamping off small blood vessels and other fluid ducts in the body. It is a further object of this invention to provide plastic hemostatic clips of both absorbable and nonabsorbable materials. It is yet a further object of this invention to provide plastic hemostatic clips which are quickly and easily applied to severed blood vessels and other fluid ducts with a single forceps-type instrument following the general technique as commonly used in applying metallic clips.

SUMMARY OF THE INVENTION

The hemostatic clips of the present invention have good in vivo strength properties and have vessel clamping surfaces with minimal or no gap between the surfaces when the clip is in the closed position to provide positive clamping of vessels and, hence, attain the desired hemostasis within the period of time of from 3 to 5 days.

The hemostatic clips of the present invention are configured so as to cause a minimum of trauma once implanted in a patient yet unexpectedly provide improved assurance that the clip will be handled and manipulated during the surgical procedure without being dropped or rendered unsterile.

Since the clips of the present invention are made from non-absorbable polymer materials such as nylon, polyproplylene, or the like, or absorbable polymer materials such as a homopolymer or copolymer of lactide and glycolide, h-dioxanone, or the like, they do not disrupt post-operative or other subsequent diagnostic procedures used on a patient such as X-ray imaging, CAT scanning, and the like. Our new clips may be rendered sterile by any of the well known sterilizable procedures such as ethylene-oxide, cobalt irradiation, and the like, depending on the specific polymers used.

The size and configuration of our new clip provides that the total amount of material used in the manufacture of a clip is kept to a minimum. Reducing the amount of foreign matter implanted in the patient allows for the use of more clips when required in a surgical procedure, yet surprisingly even with this reduced amount of material used in each individual clip, our new clip maintains all of the desired in vivo properties described above.

The new clips of the present invention are formed in a normally open position and may be easily and economically produced and manufactured by injection molding or other suitable techniques with a minimum production of seconds or poor quality clips because of malformation in the clip configuration. Also, the instrument required to apply our new clips is of a simple design and our new clips are readily applied using conventional surgical techniques.

The hemostatic clips of the present invention comprise first and second leg members joined at their proximal ends by resilient hinge means and terminating at their distal ends in latch means.

The hinge section according to the present invention is resilient; i.e., elastic memory, and acts as a spring which assists in the packaging of the clip as well as in the handling and placement of the clip. This resilience allows for slight forces to be applied to the clip while it is being packaged in order to maintain the clip in a desired position within the package. This resilience also allows the clip to snap into the jaws of a suitable applying instrument and allows the jaws to be slightly flexed during handling of the instrument without the clip becoming dislodged. As can be appreciated, this is a considerable advantage when utilizing the clip of the present invention.

Each leg member has an outer surface and a vessel clamping inner face. The vessel clamping inner face is in opposition to a vessel clamping inner face of the other leg member and when the clip is in the closed position, there is a minimal or no gap between the vessel clamping jaws. One leg member terminates at its distal end in a portion of the latch means. This portion comprises a deflectable hook member extending from the inner face of the leg member. The hook member has an inner face spaced from the inner face of the leg member and substantially parallel thereto. The end face of the hook member is beveled so as to form an acute angle with the inner face of the hook member. The greater portion of the outer surface of the leg member extending from said hook member has a substantially constant radius of curvature. In a preferred embodiment, a portion of this outer surface is parallel to the inner surface connecting the parallel inner jaws of the hook member and leg member. The other leg member terminates at its distal end in a complementary locking portion of the latch means. This portion comprises an end face of said leg member having a bevel complementary to the bevel on the end face of said hook member. The complementary bevel forms an obtuse angle with the inner face of the second leg member and is adapted to deflect the hook member and enter the space between the inner face of the hook member and the inner face of the first leg member. The greater portion of the outer surface of this leg member is substantially parallel to the inner face of the member.

The clip is closed by pivoting the leg members about the hinge means. The distal end of one leg member deflects and engages the hook member of the other leg member to lock the clip in the closed position.

The applier for the clips of the present invention comprises a forceps-type instrument wherein one jaw has a dished channel to receive and guide the distal end of the first leg of the clip, and the other jaw has a channel provided with clip engaging means to restrain the open clip against forward movement while held between the jaws of the applier.

DESCRIPTION OF DRAWINGS

FIG. 1 is a greatly enlarged view in perspective of a hemostatic clip according to the present invention.

FIG. 2 illustrates the clip of FIG. 1 clamped about a blood vessel.

FIG. 3 illustrates a forceps-type applier useful with the clips of the present invention.

FIG. 4 illustrates the clip of FIG. 1 retained in the jaws of a forceps-type clip applier.

DESCRIPTION OF PREFERRED EMBODIMENTS

Figure 5:
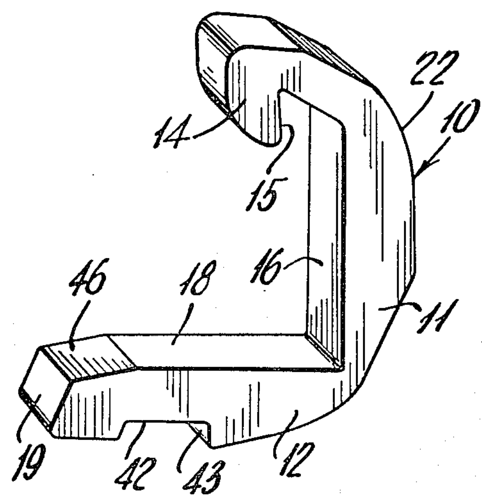
FIG. 5 illustrates a modification of the clip of FIG. 1.

Referring now to FIG. 1, there is illustrated hemostatic clip 10 constructed of two leg segments 11 and 12 connected at the proximal ends thereof by hinge section 13. Leg 11 terminates at the distal end thereof in hook member 14. Inner face 15 of hook member 14 is substantially parallel to inner face 16 of leg 11. Surface 25 of extension 17 of hook member 14 forms an obtuse angle $\alpha$ with inner face 16 of jaw 11, and acute angle $\beta$ with inner face 15 of hook 14.

Leg segment 12 has inner face 18 terminating in end surface 19 forming obtuse angle $\alpha'$ with face 18 and acute angle $\beta'$ with the outer surface 20. Surface 20 is substantially parallel to face 18 at the distal end of leg 12, but approaches face 18 at the proximal end by following the radius of curvature indicated at 21.

The outer surface at the distal end of leg 11 defines a curve of substantially constant radius extending from the hook member 14 into the body of leg 11. In the embodiment shown the first portion 17 of the constant radius area has been flattened to render it parallel to the face 25 connecting the inner face 15 of the hook member and the inner face 16 of leg member 11. Hence it can be seen that the constant radius of curvature required need not be a totally smooth curve but may be a series of flattened sections or a combination of smooth and flattened sections which overall have the same radius of curvature and extend over a greater portion; i.e., more than 50% of the outer surface of the leg member extending from the hook member to the resilient hinge. The effect of this curvature is to permit the clip to slide forward and rotate in the jaw of the applier during closure as hereafter described. The curvature also reduces the thickness of the leg at the distal end thereof to increase the flexibility of hook member 14 while maintaining strength and rigidity towards the center of the leg. The deflectability of hook 14 is further increased by the flattened first portion 17 as illustrated in FIG. 1 where outer surface 24 is made parallel to inner surface 25. Leg 11 also decreases in thickness along plane 23 extending over the proximal one-third of the leg and has a minimum thickness at the junction with leg 12 to form a hinge along line 13.

The length and width of faces 16 and 18 are substantially equal as are angles $\alpha$ and $\alpha'$, and $\beta$ and $\beta'$. Face 15 of hook 14 is spaced from face 16 of leg 11 by a distance corresponding to the thickness of leg 12 between face 18 and surface 20. When legs 11 and 12 are pivoted about hinge 13 to bring faces 18 and 16 into opposition, hook 14 is deflected by surface 19 of leg 12 until the distal end of leg 12 snaps under hook 14 and is thereby locked in place. Front surface 26 of hook 14 is preferably rounded and angled as illustrated to facilitate the passage of leg 12 during clip closure.

When the clip is closed over a tubular vessel as illustrated in FIG. 2, surfaces 16 and 18 engage and compress vessel 27 to close the lumen. Surfaces 16 and 18 may be smooth as illustrated in FIG. 1, or may be provided with ridges or grooves to increase vessel holding power. The distal end of surface 18 of leg 12 is preferably beveled as illustrated by broken line a in FIG. 1 to reduce the thickness at the tip of the leg, thereby compensating for inward deflection of hook 14 during closure which reduces the clearance between surfaces 15 and 16 and may otherwise interfere with the latching of the clip.

The significance of the clip configuration as illustrated in FIG. 1 and described above will be appreciated in connection with the instrument used to apply and close the clip as illustrated in FIG. 3 and FIG. 4.

FIG. 3 illustrates a forceps-type ligating clip applier 30 comprising two handle members 31 and 32 crossing at hinge point 33 and maintained in a normally open position by spring 38. Handle 31 extends beyond hinge 33 forming jaw member 34 while the extension of handle 32 forms jaw member 35.

FIG. 4 illustrates the detail of the construction of jaws 34 and 35 and the interaction of the jaws with the clip of FIG. 1. Jaw 35 contains dished channel 39 on the inner jaw surface extending back from the tip of the jaw. Jaw 34 is provided with dished channel 40 connecting with straight channel 41 at point 42. Channel 41 terminates in a blind end near the tip of jaw 34 forming ledge 43 which restrains leg 12 against forward movement when in position between the jaws. The widths of channels 39, 40 and 41 correspond to the width of clip 10 to prevent twisting or lateral movement of the clip when held in the jaws of the applier.

Pin 36 is mounted in jaw 34 behind and aligned with channel 40. Opening 37 centered in jaw 35 above pin 36 is of a sufficiently large diameter as illustrated in FIG. 4 to allow the free ingress and egress of pin 36 during opening and closing of the jaws.

Clip 10 is initially loaded in applier 30 in the normally open position as illustrated in FIG. 4. After moving the jaws of the applier and the clip into position over the vessel to be ligated, the jaws of the applier are closed and the clip is locked in position over the vessel as illustrated in FIG. 2. As the jaws of the applier are closed, leg 11 of clip 10 moves forward with curved surface 22 sliding and rotating in channel 39. Simultaneously, the clip moves backward until surface 23 abuts pin 36. As the clip continues to close, leg 12 pivots on fulcrum 42 with the proximal end of leg 12 dropping into channel 40 and the distal end rising from channel 41 to be engaged by hook 14. Once the clip is fully closed and locked onto the vessel, the jaws of the applier are allowed to open and the applier is withdrawn from the site to be reloaded with another clip.

Figure 6:
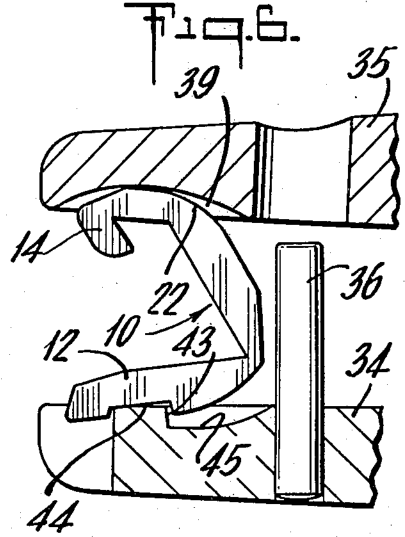
FIG. 6 illustrates the clip of FIG. 5 retained in the jaws of a clip applier.

Referring now to FIG. 5, there is illustrated a variation of the clip of FIG. 1 wherein leg 12 has been modified by the addition of indent 42 across the outer surface near the distal end thereof. The clip applier is similarly modified to accept the clip as illustrated in FIG. 6 by providing lower jaw 34 with step 44 sized to fit within indent 42. As illustrated, the distal tip of jaw 34 forward of step 44 is slotted to provide clearance for the distal tip of leg 12 and for the passage of hook 14 as the clip is closed. The clip is also illustrated with the inside face of leg 12 beveled at 46 to assure ready closure of the clip as hereinbefore described.

During closure of the clip of FIG. 5, the distal end of leg 11 moves forward with radial surface 22 of leg 11 rotating and sliding in dished channel 39 of leg 35. Leg 12 pivots on step 44 of jaw 34 and the proximal end lowers into channel 45 which conforms to the general shape of the clip. During the final stage of closure, leg 12 lies substantially stationary on jaw 34 and leg 11 pivots at the hinge point until hook 14 engages the distal end of leg 11 thereby locking the clip in a closed configuration. In this embodiment, pin 36 in the applier is generally not contacted by the clip unless the clip is dislodged from step 44 during the closure.

Figure 7:
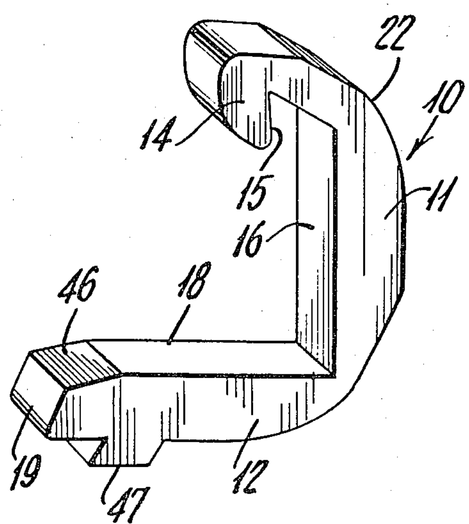
FIG. 7 illustrates a modification of the clip of FIG. 1.
Figure 8:
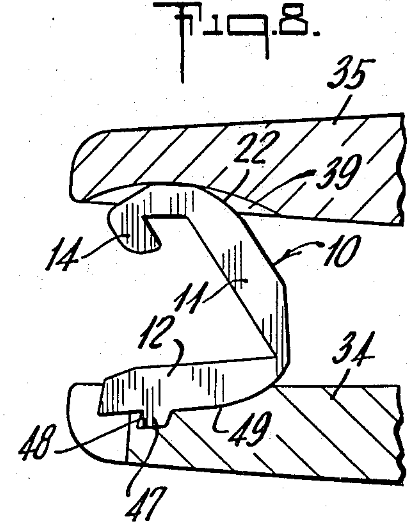
FIG. 8 illustrates the clip of FIG. 7 retained in the jaws of a clip applier.

Referring now to FIG. 7, there is illustrated another embodiment of the ligating clip of FIG. 1 wherein leg 12 is provided with lug 47, and jaw 34 of the applier is provided with channel 49 including slot 48 conforming to the outer space of leg 12. In this embodiment, leg 12 is stationary and securely set in jaw 34 of the applier and pin 36 as illustrated in FIG. 3 is unnecessary. During closure, leg 11 of clip 10 moves forward with radial surface 22 rotating and sliding in dished channel 39 of leg 35 until the distal end of leg 12 is engaged by hook 14, thereby locking the clip in position. As illustrated in FIG. 8, the distal tip of jaw 34 is slotted below the tip of leg 12 to allow hook 14 to bypass and lock with leg 11.

As further illustrated in FIG. 7 and FIG. 8, lug 47 is set back from the distal end of leg 12 by a distance corresponding to the length of inner face 15 of hook 14 to permit maximum closure of the hook when engaging leg 12. Since jaw 34 of the applier occupies a portion of the space between lug 47 and the distal end of leg 12 when the clip is in the applier, hook 14 engages the available portion of leg 12 with the tip of hook 14 abutting the end of jaw 34 as the clip is closed. As the jaws of the applier are opened after setting the clip and the clip is released therefrom, hook 14 moves to fully engage leg 12 up to lug 47.

The clips and appliers of the present invention are characterized by the structure which permits the legs of the clip to pivot about a hinge point with one leg sliding forward within the jaws of the holder during closure while the other is restrained against forward movement. This unique action of the clip is accomplished by providing one jaw of the applier with a dished channel which guides the clip without restraining its forward movement. The clip is likewise provided with a radial curvature on the outer surface at the distal end of the moving leg to permit its forward movement and rotation in the dished channel. The other jaw of the applier is provided with means interacting with the second leg of the clip to hold the clip in the applier during positioning and closure. The second leg of the clip may be held stationary on the jaw of the applier or may pivot to a limited degree during closure.

The clips of the present invention may be constructed in various sizes according to their intended function. Hemostatic clips are typically less than 6 mm in length, about 1.5 mm in width, and have a vessel clamping surface about 3 mm in length. The dimensions of the clip may be reduced by about 50 percent for certain applications in microsurgery. Larger clips for special hemostatic applications and other functions such as closure of oviducts or vas deferens may have dimensions of about double those of a typical hemostatic clip. The various sizes of clips are preferably matched with individual appliers having jaws tailored to the size of the clip for best performance.

The clips of the present invention are most conveniently molded of biologically acceptable plastic materials which may be absorbable or nonabsorbable. Preferred absorbable polymers include homopolymers and copolymers of glycolide and lactide, and p-dioxanone. Preferred nonabsorbable polymers include nylon, polyester and polypropylene. All these materials have been demonstrated to be biologically acceptable when used as sutures or other implantable medical devices. The clips may also be cast or machined from solid polymeric materials.

Many variations in the clip and applier other than the embodiments disclosed herein will be apparent to those skilled in the art and are contemplated within the scope of the present invention.

We claim:

1. A sterile, plastic, hemostatic clip comprising:

first and second leg members joined at their proximal ends by resilient hinge means and terminating at their distal ends in latch means, each leg member having an outer surface and a vessel clamping inner face, said vessel clamping inner face being in opposition to the vessel clamping inner face of the other leg member;

said first leg member having a body portion and a latch portion, said latch portion being disposed at the distal end of said leg member, said latch portion comprising a deflectable hook member extending from the inner face of said first leg member, said hook member having an inner face spaced from the inner face of said first leg member and substantially parallel thereto, said hook member having a connecting face, said connecting face being disposed at an acute angle to the inner face of said hook member and connecting to the inner face of said first leg member at an obtuse angle therewith, said hook member having an end face extending from the inner face of said hook member and and beveled so as to form an acute angle with the inner face of said hook member, the portion of said hook member containing said connecting surface immediately adjacent the body portion of said first leg member having a reduced thickness as compared to the thickness of the first leg member to improve the deflectability of said hook member;

the body portion of said first leg member between said latch portion and said hinge means comprising a center section and two side sections, said center section being the thickest part of said body portion, the outer surface of said center section being parallel to the vessel clamping inner face of said first leg member, a first side section connecting said center section to said latch portion, the outer surface of said first side section having a substantially constant radius of curvature extending from said center section to said latch portion and a second side section connecting said center section to said hinge means, the outer surface of said second side section being tapered from the center section to the resilient hinge means;

said second leg member terminating at the distal end thereof in a complementary locking portion of the latch means, said locking portion comprising an end face of said second leg member, said end face having a bevel complementary to the bevel on the end face of said hook member, said complementary bevel forming an obtuse angle with the inner face of said second leg member and adapted to deflect the said hook member and enter the space between the inner face of said hook member and the inner face of said first leg member, the greater portion of the outer surface of said leg member being substantially parallel to the inner face of said member;

whereby when said first and second leg members are pivoted about said hinge means the distal end of said second leg member deflects and engages the hook member of the first leg member to lock the clip in a closed position.

2. The hemostatic clip of claim 1 wherein said resilient hinge means is defined by a line of minimum clip thickness at the juncture of the first and second leg members.

3. A hemostatic clip of claim 1 wherein said second leg member includes a channel disposed in the outer surface of said leg member and extending across the width of the outer surface of said leg member said channel being disposed proximally from the distal end of said second leg member a distance corresponding to the length of the inner face of said hook member.

4. The hemostatic clip of claim 1 wherein said leg member includes a lug disposed from the outer surface of said second leg member and extending across the width of the outer surface of said second leg member said leg being disposed proximally from the distal end of said second leg member a distance corresponding to the length of the inner face of said hook member.

* * * * *